_United States Patent_ [19]

Lush

[11] Patent Number: 4,815,923

[45] Date of Patent: Mar. 28, 1989

[54] SWEET CORN BASED RODENTICIDE

[75] Inventor: Raymon W. Lush, Bloomfield, Nebr.

[73] Assignee: Sweet Corn Products, Bloomfield, Nebr.

[21] Appl. No.: 909,601

[22] Filed: Sep. 22, 1986

[51] Int. Cl.$^4$ .................... A01N 25/08; A01N 35/00; A01N 43/16

[52] U.S. Cl. .................... 424/410; 514/457; 514/681

[58] Field of Search ............... 424/410; 514/457, 681

[56] References Cited

U.S. PATENT DOCUMENTS

| | | | |
|---|---|---|---|
| 2,687,365 | 8/1952 | Link | 424/410 |
| 2,770,067 | 11/1956 | Lindblom | 424/410 |
| 2,900,302 | 8/1959 | Correll | 514/502 |
| 3,113,071 | 12/1963 | Derse et al. | 424/410 |
| 3,258,396 | 6/1966 | Schaar | 424/410 |
| 3,496,272 | 2/1970 | Kruger | 424/410 |

OTHER PUBLICATIONS

Jul. 1977, Publication of National Pest Control Association Entitled "Vertebrate Pests Commensal Rodents", ESPC 041253–041260.

Bell Laboratories Inc., Technical Release for Rodent Cake P.C.Q. Rat and Mouse Bait Diphacinone Concentrates.

Jap. J. Sanit. Zool., vol. 24, No. 3, pp. 207–213, 1974, Article by Tyuzi Kasano entitled "The Toxicity of Diphacinone (2-diphenylacetyl-1,3-Indandione to Laboratory Rats and Mice".

_Primary Examiner_—Allen J. Robinson
_Attorney, Agent, or Firm_—John A. Beehner

[57] ABSTRACT

A rodenticide includes an active ingredient mixed with an inert ingredient comprising dried sweet corn as a substantial portion thereof. The dried sweet corn is preferably ground, mixed with the active ingredient and pelleted, resulting in a safe yet effective rodenticide.

8 Claims, No Drawings

SWEET CORN BASED RODENTICIDE

BACKGROUND OF THE INVENTION

The present invention is directed generally to a new rodenticide composition that is universally acceptable to rats and mice and more particularly to a mixture of raw dried sweet corn as a natural palatable inert ingredient along with an effective yet safe active ingredient.

Rodents have been a serious and age-old problem for mankind. Ironically, rats and mice have more of a tendency to thrive in inhabited areas just where man does not want them. As a result of this cohabitation, man is at constant war with the rodent population and for good reason. The problems that rodents cause are numerous. Foremost are the diseases that rodents transmit to mankind by actual bites and by contamination through their urine and feces. Secondly, the economic loss caused by rats and mice is tremendous. It is estimated that about 1/5 of the foodstuffs planted every year in the world are never eaten by people because of the damage caused by rodents. In fact, in some parts of the world, rodents make it impossible to grow some very much needed crops. Rodents not only cause problems with the growing and producing of crops and foodstuffs but they also cause serious problems with processed products. The amount of contamination of food by rats and mice is easier understood when one looks at the figures. One rat alone will produce approximately 25,000 droppings per year while one mouse will produce about 18,000 droppings per year.

Rats and mice also cause millions of dollars of damage to structures and materials every year. They have an inherent sense of gnawing. As a result of this physical trait, property damage can be extensive and dangerous. Many of the fires caused by "unknown origin" in the United States are believed to have been caused by rodent damage to electrical wiring.

One method of controlling the rodent population is by using rodenticides. Many different rodenticides have been devised and made commercially available to date. A typical rodenticide includes an inert food base, an active ingredient and various additives. Such grains as field corn and oats have been used as ingredients of rodenticide food bases. "Field corn" is broadly used herein to collectively refer to the various types of corn which are normally grown for feeding livestock, such as yellow dent corn, flint corn and soft corn and, in some cases, grain sorghum. Likewise, field corn is to be distinguished from sweet corn which is referred to by its botanical name Zea Mays Saccharata and by International Feed No. 40297. Known rodenticides have had certain limitations, however, relating primarily to effectiveness and safety.

In laboratory tests reported in a publication of the National Pest Control Association, a variety of foods from several different main groups or classes were tested for their relative preference or acceptance by Norway rats. The main groups included meats, vegetables, fish, fruits, liquids and grains and seeds. In the vegetable class, those ranked in the order of their highest degree of acceptance were frozen sweet corn, frozen green peas, canned sweet corn, carrots, sweet potatoes, butternut and acorn squash. Likewise, the preferred grains and seeds included breakfast rolled oats, freshly ground whole yellow field corn, steel-cut oat groats, brown/white rice, degerminated yellow corn meal and hominy grits.

Several of the above-mentioned foods, and particularly the vegetables such as frozen sweet corn and green peas and canned sweet corn, have been considered as unsuitable ingredients for rodenticides because of short shelf life. Rodenticides are typically subjected to storage stability tests wherein a batch of the rodenticide is tested periodically such as monthly over a one year period to determine if the food base is shelf stable and if the active ingredient is still active.

Rodent acceptance depends upon a combination of texture, taste and odor. Whereas odor can help attract a rodent to a bait, the final test of consumption is the palatability of the material determined by its taste and texture.

A common solution for improving rodenticides is to include additives. Additives may be included for many different reasons but often result in increased acceptance of the rodenticide. Additives may include an odor-producing attractant, binders for holding the bait particles together, coloring agents, emetics for causing non-target animals to regurgitate the bait, enhancers such as sugar, preservatives and, to a limited extent, potentiating agents. Such additives can increase manufacturing costs without an attendant increase in the acceptance rate for the rodenticide product.

An important design criteria for a rodenticide is its relative safety. Warfarin has been widely accepted over the last two decades as an indirect anticoagulant rodenticide for rat control in urban and rural areas because of the safety to non-target animals and high control efficiency to rodents. Its effectiveness is limited, however, since a long treatment period, over two weeks, is required to obtain satisfactory results and Warfarin-resistant rats and mice have been discovered in the United States and abroad. Acute active ingredients, such as strychnine, are available but they are generally considered too dangerous for common usage. A second generation of active ingredients has been developed which require only a single feeding so that the rodents do not have to eat as much of the rodenticide but these can also pose safety threats to humans and non-target animals.

Accordingly, a primary object of the present invention is to provide an improved rodenticide.

Another object is to provide a rodenticide which is relatively safe to use and which is highly effective for rodent control.

Another object is to provide such a rodenticide which is simple and economical to formulate and produce.

Another object is to provide a rodenticide which uses dried natural sweet corn as the inert ingredient thereof.

Another object is to provide a highly effective rodenticide which is free of additives.

Another object is to provide a safe rodenticide for which a known antidote is available for the active ingredient thereof.

Finally, an object of the invention is to provide an improved rodenticide which is simple in formulation, economical to produce and effective in operation.

SUMMARY OF THE INVENTION

The improved rodenticide of the present invention includes an active ingredient mixed with an inert ingredient including natural raw, dried sweet corn as a substantial portion thereof. Preferably the sweet corn is dried down to a dented state either in the field or by artificial means after harvesting. The dried sweet corn is then ground and mixed with a relatively safe active ingredient such as diphacinone and pelleted for distribution and use in pellet form. Rodenticides including dried natural raw sweet corn as the inert ingredient thereof according to the invention have been found to have uncommonly high acceptance by rats and mice as demonstrated by standard efficacy tests. While sweet corn may be economically produced, additional economies are achieved because the dried sweet corn-based rodenticide requires no expensive additives. A relatively, safe active ingredient such as diphacinone is preferred. The effectiveness of such moderate active ingredient is greatly enhanced by the high acceptance ratings of raw sweet corn which assures that sufficient quantities of the rodenticide will be consumed for effective rodent control.

DESCRIPTION OF THE PREFERRED EMBODIMENT

The improved rodenticide of the present invention is a mixture of an active ingredient with an inert ingredient including raw dried sweet corn as the substantial portion thereof. Zea Mays Saccharata is the botanical name for sweet corn which is also referred to by International Feed No. 40297. Sweet corn is normally grown for human consumption and is harvested in the ear while the kernel is in the relatively soft and moist milk stage. The soft and moist sweet corn has limited utility for a rodenticide because of its short shelf life due to spoilage and the difficulty of handling, dividing and mixing the soft and moist kernels.

For use in the present invention, however, sweet corn is dried down to a dented state. Dried sweet corn herein refers to sweet corn having a moisture content of 15% or less. A moisture content of 10% or below is preferred.

The sweet corn may be planted and cultivated in the same manner as field corn and is left in the field to mature past the milk stage, which is the normal harvest period for sweet corn. It is left in the field to mature as long as possible to allow maximum dry down of the kernel before ear droppage and stalk lodging occurs to the point that it is no longer economically feasible to harvest.

The dried sweet corn is then ground to a fine ground condition which is not nearly as fine as flour, for example. "Grinding" herein collectively refers to such processes as crushing, grinding, rolling or otherwise reducing the kernel to a smaller particle size, with the end result hereinafter referred to as ground sweet corn. A double grinding process is preferred for a more uniform particle size in the dried ground sweet corn.

The ground sweet corn is then mixed with an active ingredient so as to be effective as a rodenticide. A preferred active ingredient is diphacinone. The chemical name is 2-(diphenylacetyl)-1,3-indandione. It has the appearance of pale yellow crystals. It is preferred for its effectiveness and safety. Vitamin K-1 is a known antidote for this active ingredient. Diphacinone is an anticoagulant which depresses the hepatic synthesis of substances essential to blood clotting (prothrombin). The anti-prothrombin effect results in widespread internal hemorrhage.

The diphacinone should comprise between 0.001 and 0.01 percent of the mixture by weight. Fifty parts per million diphacinone (0.005%) is preferred.

The mixture is preferably pelleted for use as a rodenticide. The optimal particle size for Norway and Roof rats lies between 0.5 and 1.5 millimeters. Mice prefer a somewhat smaller size. It is anticipated that the rodenticide of the present invention will be formed in pellets having a 3/16 inch diameter with approximately 7 pellets per gram or 196 pellets per ounce.

The effectiveness of a rodenticide is generally measured by standard efficacy tests. In the EPA efficacy test designed by the Environmental Protection Agency, rats are presented with two baits, namely the bait being tested and a second bait consisting of the EPA challenge diet. The latter bait comprises 65% yellow dent corn, 25% rolled oats, 5% corn oil and 5% sugar, with no active ingredient. For a rodenticide to pass the EPA efficacy test, it must constitute 33% of the total diet of the test rats and result in at least a 90% mortality. Test results for commercially available rodenticides commonly turn up diet percentages of approximately 40% or below. Fifty percent (50%) is regarded as exceptional. Test results for the rodenticide of the present invention as applied to rats resulted in a showing of 54.7% of total diet with 100% mortality. As applied to mice, the results showed 47.9% total diet with 95% mortality.

The above results were achieved despite the very simple formulation of the present invention as including only two ingredients. Rodenticides typically include multiple grains, oils and sugars. Natural raw sweet corn is sufficiently high in oil and sugar content so as to eliminate the need for such additives. In this connection, it is preferred that the sweet corn be used in a raw state, meaning unprocessed. Cooking processes such as roasting alters the starch content by converting some starches to sugar resulting in an over sweet rodenticide with diminished acceptance by rodents.

Thus, there has been shown and described an improved rodenticide which accomplishes all of the stated objects.

I claim:

1. A rodenticidal composition comprising, an effective amount of a rodenticide and an inert ingredient comprising dried sweet corn as a substantial portion thereof.

2. The composition of claim 1 wherein said inert ingredient is comprised entirely of dried sweet corn.

3. The composition of claim 1 wherein said sweet corn is in a raw state.

4. The composition of claim 3 wherein said inert ingredient is free of additives.

5. The composition of claim 3 wherein said sweet corn is ground, mixed with the rodenticide and pelleted.

6. The composition of claim 5 wherein the pelleted rodenticide is formed in pellets generally having a diameter between 3 and 6 millimeters.

7. The composition of claim 3 wherein said rodenticide is diphacinone.

8. The composition of claim 3 wherein the rodenticide comprises between 0.001 and 0.010 percent by weight.

* * * * *